US00PP12776P2

(12) United States Plant Patent
Takishita

(10) Patent No.: US PP12,776 P2
(45) Date of Patent: Jul. 16, 2002

(54) DIEFFENBACHIA PLANT NAMED 'HATSUKO'

(76) Inventor: Howard Y. Takishita, 2566 Haupoa Pl., Haiku, HI (US) 96708

( * ) Notice: Subject to any disclaimer, the term of this patent is extended or adjusted under 35 U.S.C. 154(b) by 15 days.

(21) Appl. No.: 09/801,597

(22) Filed: Mar. 9, 2001

(51) Int. Cl.[7] ..... A01H 5/00
(52) U.S. Cl. ..... Plt./378

(58) Field of Search ..... Plt./378

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Dieffenbachia plant named 'Hatsuko', characterized by its upright and outwardly growth habit with large leaves; freely clumping habit, full and dense plants; and unique green and whitish green variegated leaves and petioles.

2 Drawing Sheets

BACKGROUND OF THE INVENTION

The present Invention relates to a new and distinct cultivar of Dieffenbachia plant, botanically known as *Dieffenbachia picta* and hereinafter referred to by the name 'Hatsuko'.

The new Dieffenbachia is a naturally-occurring whole plant mutation of an unnamed selection of *Dieffenbachia picta*, not patented. The new Dieffenbachia was discovered by the Inventor in 1981 in a controlled environment in Haiku, Hi., as a single plant within a population of plants of the unnamed selection of *Dieffenbachia picta*.

Asexual propagation of the new cultivar by tissue-culture in Haiku, Hi., has shown that the unique features of this new Dieffenbachia are stable and reproduced true to type in successive generations.

SUMMARY OF THE INVENTION

The following traits have been repeatedly observed and are determined to be the unique characteristics of 'Hatsuko'. These characteristics in combination distinguish 'Hatsuko' as a new and distinct cultivar:

1. Upright and outwardly arching growth habit with large leaves.
2. Freely clumping habit, full and dense plants; typically about 10 offshoots per plant.
3. Unique green and whitish green variegated leaves and petioles.

In side-by-side comparisons conducted by the Inventor in Haiku, Hi., plants of the new Dieffenbachia differed from plants of the parent selection of *Dieffenbachia picta* in the following characteristics:

1. Plants of the new Dieffenbachia are freely-clumping and produce more offshoots per plant than plants of the parent selection.
2. Plants of the new Dieffenbachia have more leaves and are more dense than plants of the parent selection.
3. Plants of the new Dieffenbachia have thicker main stems than plants of the parent selection.
4. Leaves of plants of the new Dieffenbachia and of the parent selection differ in variegation pattern.

Plants of the new Dieffenbachia can be compared to plants of the *Dieffenbachia picta* cultivar Rudolph Roehrs, not patented. However in side-by-side comparisons conducted by the Inventor in Haiku, Hi., plants of the new Dieffenbachia differed from plants of the cultivar Rudolph Roehrs in the following characteristics:

1. Plants of the new Dieffenbachia are freely-clumping and produce more offshoots per plant than plants of the cultivar Rudolph Roehrs.
2. Plants of the new Dieffenbachia have more leaves and are more dense than plants of the cultivar Rudolf Roehrs.
3. Plants of the new Dieffenbachia have stronger main stems than plants of the cultivar Rudolph Roehrs.
4. Leaves of plants of the new Dieffenbachia and of the cultivar Rudolph Roehrs differ in variegation pattern.

Plants of the new Dieffenbachia can also be compared to plants of the *Dieffenbachia picta* cultivar Camille, not patented. However in side-by-side comparisons conducted by the Inventor in Haiku, Hi., plants of the new Dieffenbachia differed from plants of the cultivar Camille in the following characteristics:

1. Plants of the new Dieffenbachia are larger than plants of the cultivar Camille.
2. Plants of the new Dieffenbachia have larger leaves than plants of the cultivar Camille.
3. Plants of the new Dieffenbachia have variegated petioles whereas plants of the cultivar Camille have non-variegated petioles.
4. Leaves of plants of the new Dieffenbachia and of the cultivar Camille differ in variegation pattern.

The cultivar Hatsuko has not been observed under all possible environmental conditions. The phenotype may vary somewhat with variations in environment such as temperature, light intensity and/or fertilizer rate, without, however, any variance in genotype.

BRIEF DESCRIPTION OF THE PHOTOGRAPHS

The accompanying colored photographs illustrate the overall appearance of the new Dieffenbachia, showing the colors as true as it is reasonably possible to obtain in colored reproductions of this type. Colors in the photographs may differ slightly from the color values cited in the detailed botanical description which accurately describe the colors of the new Dieffenbachia.

The photograph on the first sheet comprises a side perspective view of a typical plant of 'Hatsuko'.

The photographs on the second sheet comprise close-up views of the upper surface of a typical leaf (top photograph) and the lower surface of a typical leaf (bottom photograph). Plants used in the photographs were similar in age to those used in the following detailed botanical description.

DETAILED BOTANICAL DESCRIPTION

In the following observations, measurements and values describe plants of the new Dieffenbachia grown in 20-cm containers, in Haiku, Hi., in a fiberglass-covered greenhouse with day temperatures about 24° C., night temperatures about 18° C., and with shading providing a 73 percent reduction in ambient light levels. Plants used for this description were grown in the containers for about ten to twelve months. Color references are made to The Royal Horticultural Society Colour Chart, 1995 edition, except where general terms of ordinary dictionary significance are used.

Botanical classification: *Dieffenbachia picta* cultivar Hatsuko.

Parentage: Naturally-occurring whole plant mutation of an unnamed selection of *Dieffenbachia picta*, not patented.

Propagation:

*Type.*—By tissue-culture.

*Time to initiate roots on a tissue-cultured plantlet.*—Summer: About 30 days at 24° C. Winter: About 42 days at 18° C.

*Time to produce a rooted plant from a tissue-culture plantlet.*—Summer: About 42 days at 24° C. Winter: About 56 days at 18° C.

*Root description.*—Thick, freely-branching, white and fleshy.

Plant description:

*Appearance.*—Upright and outwardly arching.

*Plant height.*—About 110 cm.

*Plant width.*—About 70 cm.

*Growth rate/vigor.*—Vigorous.

*Stem color.*—Darker than 144A.

*Branching habit.*—Freely clumping habit; plants typically produce about 10 offshoots per plant; full and dense plants.

*Foliage description.*—Length: About 34 cm. Width: About 18.5 cm. Shape: Oblong to somewhat ovate. Apex: Cuspidate. Base: Slightly cordate. Margin: Entire. Orientation: Initially upright to outwardly arching to somewhat drooping. Surface: Flat, rugose. Texture: Smooth, glabrous; leathery. Midrib: Prominent on the lower surface. Primary veins: Recessed on upper surface and prominent on lower surface. Color: Dark green margins and midvein with whitish green centers; random light green spots towards the margins and random dark green splotches and light green speckles radiating from the margins toward the center. Upper surface: Margins: Dark green, darker and more green than 147A. Random yellow green, close to 154A, spots towards the margins. Center: Light green, mostly 144A, 144B and 144C; towards midvein, whitish green, lighter than 144C to white, 155D. Random dark green, darker than 147A, splotches. Midvein: Dark green, darker and more green than 147A. Random small light green, close to 144A to 144B, speckles. Lower surface: Margins: Green, close to 147A to 147B. Random white spots, close to 155D, towards margins. Center: Very light green to white, 145D to 155D. Midvein: White, 155D. Petiole: Length: About 18 cm. Diameter, at base: About 3.3 cm. Diameter, just above wing: About 1.1 cm. Diameter, just below leaf: About 8 mm. Length of wing: About 13 cm. Width of wing: About 5 mm. Color: Upper surface: Dark green, close to 147A, with random white, 155D, speckles. Lower surface: White, 155D.

Inflorescence description: Inflorescence development has not been observed on plants of the new Dieffenbachia grown under greenhouse production conditions.

Disease resistance: Resistance to pathogens common to Dieffenbachia has not been observed on plants of the new Dieffenbachia.

Temperature tolerance: Plants of the new Dieffenbachia have been observed to tolerate temperatures from 0 to 43° C.

It is claimed:

1. A new and distinct cultivar of Dieffenbachia plant named 'Hatsuko', as illustrated and described.

* * * * *

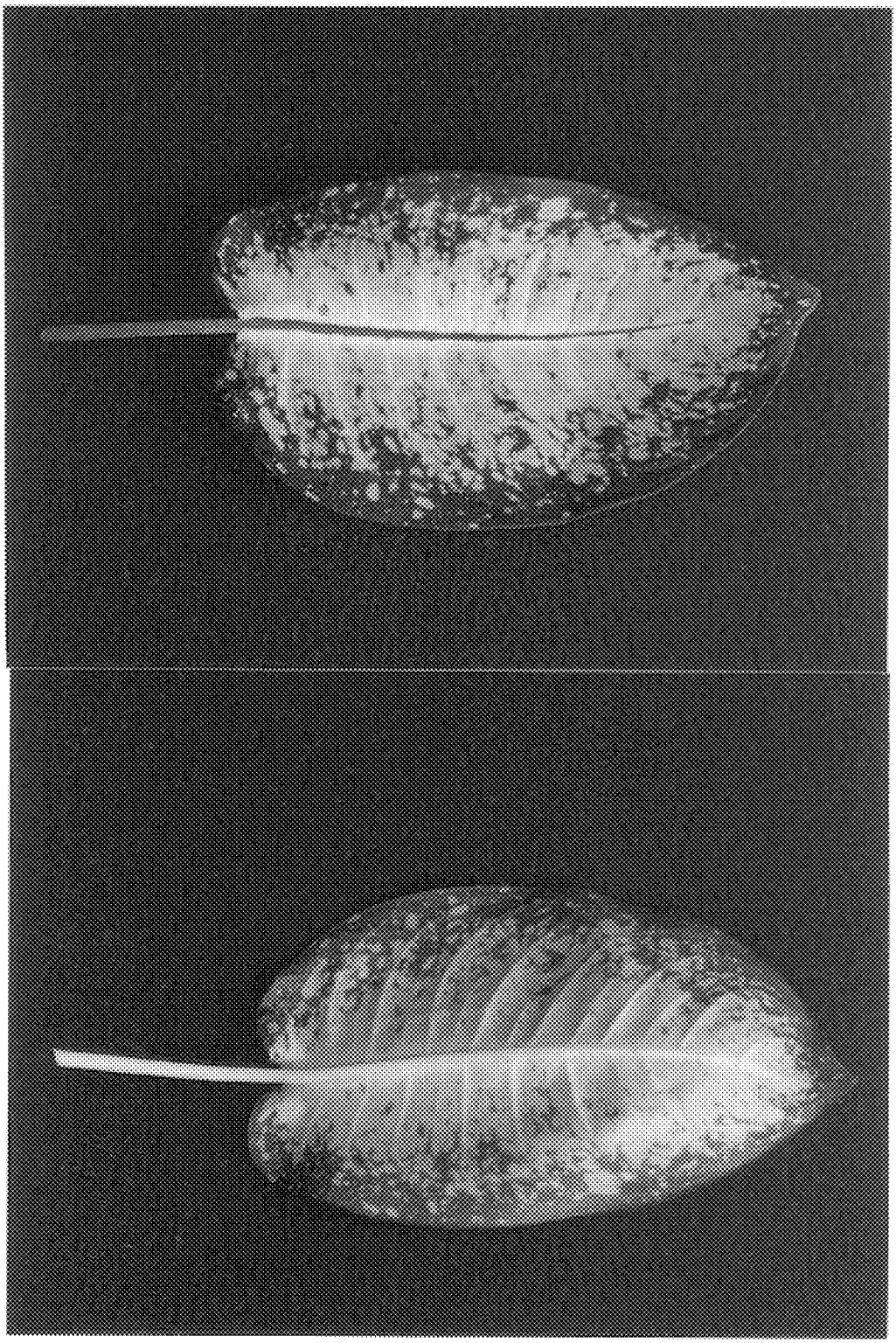

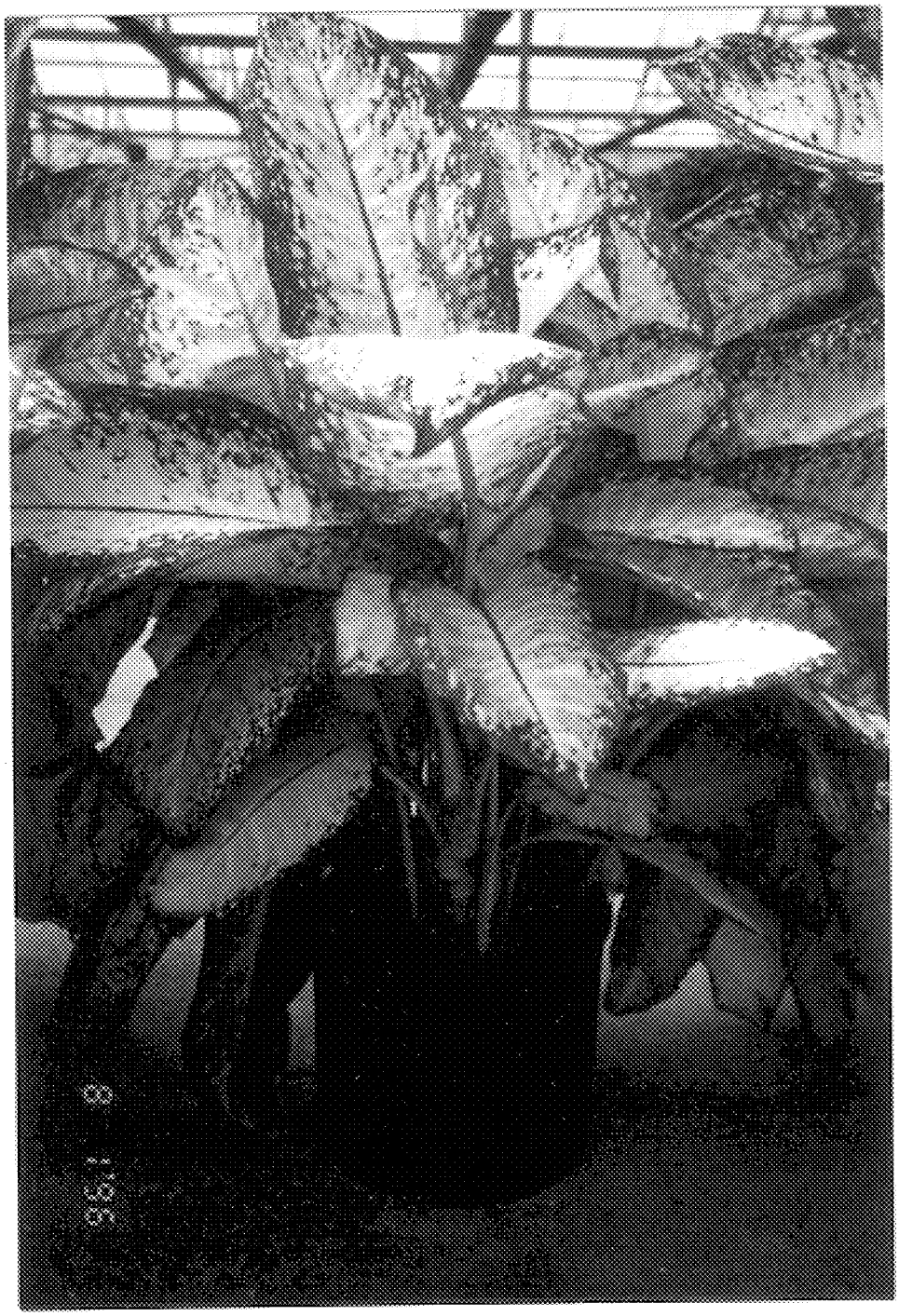
8
1996